United States Patent [19]
Falk et al.

[11] Patent Number: 5,817,642
[45] Date of Patent: Oct. 6, 1998

[54] CLEARING OF ATHEROSCLEROSIS

[75] Inventors: Rudolf Edgar Falk; Samuel Simon Asculai, both of Toronto, Canada

[73] Assignee: Hyal Pharmaceutical Corporation, Mississauga, Canada

[21] Appl. No.: 464,769

[22] PCT Filed: Apr. 27, 1995

[86] PCT No.: PCT/CA95/00243

§ 371 Date: Aug. 15, 1995

§ 102(e) Date: Aug. 15, 1995

[87] PCT Pub. No.: WO95/29683

PCT Pub. Date: Nov. 9, 1995

Related U.S. Application Data

[63] Continuation-in-part of Ser. No. 675,908, Jul. 3, 1991.

[30] Foreign Application Priority Data

Apr. 29, 1994 [CA] Canada .................................. 2122551

[51] Int. Cl.⁶ .................................................. A61K 31/70
[52] U.S. Cl. ............................................. 514/54; 536/55.1
[58] Field of Search ............................ 574/54; 536/55.1, 536/55.3

[56] References Cited

FOREIGN PATENT DOCUMENTS 0433817  6/1991  European Pat. Off. .
A-94 07505  4/1994  WIPO .

OTHER PUBLICATIONS

Falk, R. Round Table Ser. R. Soc. Med., No. 33, 1994 pp. 2–10.
H. Beyer et al., 'Lehrbueh der Organischer Chemie' 1976, S. Hirzel Verlag, Stuttgart, FRG, p. 366.
J.E.F. Reynolds 'Martindal, The Extra Pharmacopoeia' 1993.

*Primary Examiner*—Elli Peselev
*Attorney, Agent, or Firm*—Ivor M. Hughes; Neil H. Hughes; Marcelo K. Sarkis

[57] ABSTRACT

A method of clearing atherosclerosis comprising the step of administering to a patient, at least one dosage amount of a pharmaceutical composition comprising an effective non-toxic amount of each of a chelating agent, a non-steroidal anti-inflammatory drug (NSAID), an anti-oxidant and a form of hyaluronic acid, selected from hyaluronic acid, salts thereof, homologues, analogues, derivatives, esters, complexes, fragments and subunits.

16 Claims, No Drawings

CLEARING OF ATHEROSCLEROSIS

This is a Continuation-In-Part application of U.S. patent application Ser. No. 07/675,908, first filed under the PCT (Patent Cooperation Treaty) application Ser. No. PCT/CA90/00306 filed on the 18th day of Sep., 1990 (claiming priority from Canadian patent application Ser. No. 612,307 filed the 21st day of Sep., 1989) and entering the National Phase in the United States on the 3rd day of Jul., 1991.

FIELD OF INVENTION

This invention relates to the treatment of arterial disease and pharmaceutical compositions suitable for such use. Particularly the invention relates to the clearing of atherosclerosis.

BACKGROUND OF THE INVENTION

Atherosclerosis is prevalent in the North American population believed to be caused in part by a diet rich in cholesterol. Over the years, deposits of yellowing plaques (atheromos) containing for example cholesterol, other lipoid material, lipophages and/or other substances build up on the inner wall of the arteries (for example within the intima of large and medium-sized arteries) of a person causing the arteries to narrow inhibiting the free flow of blood. That person thus increases his/her risk of becoming a heart attack and/or stroke victim.

Balloon angioplasty is a widely accepted method of opening blockages in the coronary arteries. However in some patients after successful treatment by balloon angioplasty, arterial restenosis occurs. This time however the narrowing of the inner diameter (ID) of the artery is caused by growth (proliferation) of endothelial cells in the areas of irritation caused by the balloon angioplasty. Thus reblockage occurs not by cholesterol build-up but by build up of endothelial cells on the inner wall of the artery reducing the inner diameter (ID) of the artery leading to an infarct. This narrowing of the inner diameter (ID) of tubular walls or proliferation of cells is not however restricted or limited to the coronary arteries. It can also occur post operatively causing restenosis in for example peripheral vascular systems.

It is therefore an object of this invention to provide a new method of clearing atherosclerosis.

It is a further object of the invention to provide a new method of clearing the arteries of atheromos containing for example cholesterol, other lipoid material, lipophages and/or other substances.

It is a further object of this invention to provide pharmaceutical compositions suitable for use in such methods of treatment.

It is still a further object of this invention to provide dosage amounts of the pharmaceutical composition suitable for use in such methods of treatment.

Further and other objects of the invention will be realized by those skilled in the art from the following.

In accordance with the invention, Applicants have provided a new method and treatment of clearing atherosclerosis in which deposits of plaques (atheromos) containing cholesterol, other lipoid material, lipophages and other substances have built up within the arterial walls of a patient for example within the intima of large and medium-sized arteries. The method of treatment comprises administering for example, intravenously to a patient, at least one dosage amount of a pharmaceutical composition formulated according to embodiments of the invention. While the number and timing of administration of each dosage amount varies from patient to patient, dosage amounts administered over a number of weeks (for example 2–12 weeks) at intervals of for example two–three days from one administration to the next administration are suitable. One patient was given 45 treatments over a 5–6 week period in equal intervals. Another patient required only two treatments. Still another patient received dosage amounts intravenously over a period of 12 weeks at two dosage amounts per week. The dosage amounts comprise an effective non-toxic amount of each of a chelating agent, for example and preferably EDTA (common name for ethylenediaminetetraacetic acid), a non-steroidal anti-inflammatory drug (NSAID) (for example diclofenac, tromethamine salt of ketoralac (sold under the trade mark Toradol), indomethacin, piroxicam, ibuprofen), an anti-oxidant (for example and preferably vitamin C) and a form of hyaluronic acid, selected from hyaluronic acid, salts thereof (for example the sodium salt), homologues, analogues, derivatives, esters, complexes, fragments and subunits. The form of hyaluronic acid is preferably sodium hyaluronate having a molecular weight of less than about 750,000 daltons, for example a molecular weight of about 150,000 to 225,000 daltons.

Suitable dosage amounts may each comprise:
  (i) about 1–3 gm of the chelating agent/70 kg person (for example 3 gm of EDTA);
  (ii) about 15—30 mg of an NSAID (for example 30 mg of diclofenac sodium or the tromethamine salt of ketoralac (Toradol);
  (iii) about 12–50 gm anti-oxidant (for example in one embodiment 12.5 gm of vitimin C and in another embodiment 25 gm of vitamin C); and
  (iv) between about 50 mg to well in excess of 1000 mg of the form of hyaluronic acid (because for example of a lack of toxicity of for example sodium hyaluronate), for example in one dosage amount in excess of 200 mg per dosage amount (and in another dosage amount, 100–120 mg sodium hyaluronate having a molecular weight of about 150,000–25,000 daltons);

in sterile water (for example 200 ml of sterile water for intravenous administration).

Other suitable dosage amounts may be selected depending on the patient. Treatment may also vary and in some instances may be administered one day after another, in one day intervals or in other instances, over alternate days. Of 6 patients treated, they averaged 10–15 treatments. All of the patients had subjective improvement in function, improved arterial blood flow by Doppler in affected vessels, and clearing of occlusion by angiography.

Suitable forms of sodium hyaluronate may include a fraction supplied by Hyal Pharmaceutical Corporation supplied in a 15 ml vial of sodium hyaluronate 20mg/ml (300mg/vial—Lot 2F3). The sodium hyaluronate fraction is a 2% solution with a mean average molecular weight of about 225,000. The fraction also contains water q.s. which is triple distilled and sterile in accordance with the U.S.P. for injection formulations. The vials of hyaluronic acid and/or salts thereof may be carried in a Type 1 borosilicate glass vial closed by a butyl stopper which does not react with the contents of the vial.

The fraction of hyaluronic acid and/or salts thereof (for example sodium salt) and homologues, analogues, derivatives, complexes, esters, fragments, and sub-units of hyaluronic acid, preferably hyaluronic acid and salts thereof, may comprise hyaluronic acid and/or salts thereof having the following characteristics:

a purified, substantially pyrogen-free fraction of hyaluronic acid obtained from a natural source having at least one characteristic selected from the group (and preferably all characteristics) consisting of the following:

i) a molecular weight within the range of 150,000–225,000;

ii) less than about 1.25% sulphated mucopolysaccharides on a total weight basis;

iii) less than about 0.6% protein on a total weight basis;

iv) less than about 150 ppm iron on a total weight basis;

v) less than about 15 ppm lead on a total weight basis;

vi) less than 0.0025% glucosamine;

vii) less than 0.025% glucuronic acid;

viii) less than 0.025% N-acetylglucosamine;

ix) less than 0.0025% amino acids;

x) a UV extinction coefficient at 257 nm of less than about 0.275;

xi) a UV extinction coefficient at 280 nm of less than about 0.25; and xii) a pH within the range of 7.3–7.9. Preferably, the hyaluronic acid is mixed with water and the fraction of hyaluronic acid has a mean average molecular weight within the range of 150,000–225,000. More preferably, the fraction of hyaluronic acid may comprise at least one characteristic selected from the group (and preferably all characteristics) consisting of the following characteristics:

i) less than about 1% sulphated mucopolysaccharides on a total weight basis;

ii) less than about 0.4% protein on a total weight basis;

iii) less than about 100 ppm iron on a total weight basis;

iv) less than about 10 ppm lead on a total weight basis;

v) less than 0.00166% glucosamine;

vi) less than 0.0166% glucuronic acid;

vii) less than 0.0166% N-acetylglucosamine;

viii) less than 0.00166% amino acids;

x) a UV extinction coefficient at 257 nm of less than about 0.23;

xi) a UV extinction coefficient at 280 nm of less than 0.19; and xii) a pH within the range of 7.5–7.7

Aplicants also propose to use sodium hyaluronate produced and supplied by LifeCore™ Biomedical, Inc., having the following specifications:

| Characteristics | Specification |
| --- | --- |
| Appearance | White to cream colored particles |
| Odor | No perceptible odor |
| Viscosity Average Molecular Weight | <750,000 Daltons |
| UV/Vis Scan, 190–820 nm | Matches reference scan |
| OD, 260 nm | <0.25 OD units |
| Hyaluronidase Sensitivity | Positive response |
| IR Scan | Matches reference |
| pH, 10 mg/g solution | 6.2–7.8 |
| Water | 8% maximum |
| Protein | <0.3 mcg/mg NaHy |
| Acetate | <10.0 mcg/mg NaHy |
| Heavy Metals, maximum ppm | |
| As  Cd  Cr  Co  Cu  Fe  Pb  Hg  Ni | |
| 2.0  5.0  5.0  10.0  10.0  25.0  10.0  10.0  5.0 | |
| Microbial Bioburden | None observed |
| Endotoxin | <0.07EU/mg NaHy |
| Biological Safety Testing | Passes Rabbit Ocular Toxicity Test |

Another form of sodium hyaluronate is sold under the name Hyaluronan HA-M5070 by Skymart Enterprises, Inc. having the following specifications:

| Specifications' Test Results | |
| --- | --- |
| Lot No. | HG1004 |
| pH | 6.12 |
| Condroitin Sulfate | not detected |
| Protein | 0.05% |
| Heavy Metals | Not more than 20 ppm |
| Arsenic | Not more than 2 ppm |
| Loss on Drying | 2.07% |
| Residue on Ignition | 16.69% |
| Intrinsic Viscosity | 12.75 dl/s (XW: 679,000) |
| Nitrogen | 3.14% |
| Assay | 104.1% |
| Microbiological Counts | 80/g |
| E. coli | Negative |
| Mold and Yeast | Not more than 50/g |

Other forms of hyaluronic acid and/or its salts, and analogues, homologues, derivatives, complexes, esters, fragments and sub units of hyaluronic acid may be chosen from other suppliers, for example those described in prior art documents provided the form of hyaluronic acid chosen is suitable for transport of the medicine.

The following references teach hyaluronic acid, sources thereof, and processes for the manufacture and recovery thereof which may prove to be suitable.

U.S. Pat. No. 4,141,973 teaches hyaluronic acid fractions (including sodium salts) having:

"(a) an average molecular weight greater than about 750,000, preferably greater than about 1,200,000 —that is, a limiting viscosity number greater than about 1400 $cm^3/g.$, and preferably greater than about 2000 $cm^3/g.$;

(b) a protein content of less than 0.5% by weight;

(c) ultraviolet light absorbance of a 1% solution of sodium hyaluronate of less than 3.0 at 257 nanometers wavelength and less than 2.0 at 280 nanometers wavelength;

(d) a kinematic viscosity of a 1% solution of sodium hyaluronate in physiological buffer greater than about 1000 centistokes, preferably greater than 10,000 centistokes;

(e) a molar optical rotation of a 0.1 -0.2% sodium hyaluronate solution in physiological buffer of less than −11 X 103 degree -$cm^2$/mole (of disaccharide) measured at 220 nanometers;

(f) no significant cellular infiltration of the vitreous and anterior chamber, no flare in the aqueous humour, no haze or flare in the vitreous, and no pathological changes to the cornea, lens, iris, retina, and choroid of the owl monkey eye when one milliliter of a 1% solution of sodium hyaluronate dissolved in physiological buffer is implanted in the vitreous replacing approximately one-half the existing liquid vitreous, said HUA being (g) sterile and pyrogen free and (h) non-antigenic."

Canadian Letters Patent 1,205,031 (which refers to U.S. Pat. No. 4,141,973 as prior art) refers to hyaluronic acid fractions having average molecular weights of from 50,000 to 100,000; 250,000 to 350,000; and 500,000 to 730,000 and discusses processes of their manufacture.

While EDTA is the preferred chelating agent, other suitable chelating agents may be used such as Desferal (tm) which is deferoxamine methanesulfonate. Desferal comes in vials, Applicants believe, of 500 mg and 2 gm.

The NSAID, Applicants believe, blocks production of prostaglandin II and thromboxane. The anti-oxidant, Applicants believe, promotes prostacycline production. Thus, any substance which promotes postacycline production may be suitable as an anti-oxidant.

To reduce/prevent pain in the patient's vein during infusion of the intravenously administered dosage amount, 5–20 cc of a local anesthetic (for example xylocaine (2%)) may be added to the dosage amount. Twenty (20) cc of 5% bicarbonate of soda may also be added to the dosage amount.

According to another aspect of the invention the new method of treatment of clearing atherosclerosis (clearing atheromos) employs new combinations of therapeutic agents in dosage amounts, the new dosage amounts each comprising a chelating agent, an NSAID, an antioxidant and a form of hyaluronic acid selected from hyaluronic acid, salts thereof (for example sodium hyaluronate), homologues, analogues, derivatives, complexes, esters, fragments and subunits in a suitable carrier, for example sterile water, for intravenous use. The dosage amounts are preferably packaged in intravenous bags for single dose administration to a patient. Suitable amounts of the therapeutic agents may comprise those previously indicated or others that may be understood by those skilled in the art from reading this specification. Thus, the therapeutic agents may comprise:

(i) about 1–3 gm of the chelating agent/70 kg person (for example 3 gm of EDTA);

(ii) about 15–30 mg of an NSAID (for example 30 mg of diclofenac sodium);

(iii) about 12–50 gm anti-oxidant (for example 12.5 gm of sodium ascorbate); and (iv) about 50 mg to in excess of 1000 mg (because of a lack of toxicity) of a form of hyaluronic acid (for example 100–120 mg sodium hyaluronate having a molecular weight of about 150,000–225,000 daltons); in sterile water (for example, 200 ml).

According to another aspect of the invention, the use of (i) about 1–3 gm of the chelating agent/70 kg person (for example 3 gm of EDTA);

(ii) about 15–30 mg of an NSAID (for example 30 mg of diclofenac sodium;

(iii) about 12–50 gm anti-oxidant (for example 12.5 gm of sodium ascorbate; and (iv) about 50 mg to in excess of 1000 mg (because of a lack of toxicity) of a form of hyaluronic acid (for example 100–120 mg sodium hyaluronate having a molecular weight of about 150,000–225,000 daltons);

is provided for the treatment of atherosclerosis for clearing atheromos comprising cholesterol and other substances (plaque) from the arterial walls.

According to another aspect of the invention the use of (i) about 1–3 gm of the chelating agent/70 kg person (for example 3 gm of EDTA);

(ii) about 15–30 mg of an NSAID (for example 30 mg of diclofenac sodium;

(iii) about 12–50 gm anti-oxidant (for example 12.5 gm of sodium ascorbate; and (iv) about 50 mg to in excess of 1000 mg (because of a lack of toxicity) of a form of hyaluronic acid (for example 100–120 mg sodium hyaluronate having a molecular weight of about 150,000–225,000 daltons);

is provided in the manufacture of a pharmaceutical composition for systemic (preferably intravenous) administration for the treatment of atherosclerosis.

When the dosage amounts are administered to patients with advanced arterial disease over the time periods referred to, the patients have shown significant improvement in symptoms. The patients were assessed by angiography and their blood flow by Doppler where possible. Patients for example received 15–30 treatments of the following drug combination:

3 gm EDTA 15 mg toradol or diclofenac 12.5 gm sodium ascorbate 50 mg sodium hyaluronate (molecular weight less than about 750,000daltons usually about 225,000 daltons)

in sterile water, by intravenous administration for 2–4 days.

In two patients, the occlusions cleared and the patients have returned to a normal angiogram.

In one patient, suffering angina after receiving 45 treatments over 5–6 weeks, the patient no longer suffers any symptoms of angina.

Another patient who was treated with 25 treatments, administered twice weekly, no longer suffers any pain in his legs. Another patient who almost had heart failure in response to bronchial infection, is now after treatment, assymtematic.

Where the anti-oxidant is sodium ascorbate (vitamin C), the vitamin C it is thought reduces (trims) the size (the length) of the form of hyaluronic acid, reducing its molecular weight.

As many changes can be made to the methods of treatment, pharmaceutical compositions, and dosage amounts of the pharmaceutical composition used without departing from the scope of the invention, it is intended that all material contained herein be interpreted as illustrative of the invention and not in a limiting sense.

The embodiments of the invention in which an exclusive property or privilege is claimed are as follows:

1. A method of clearing atherosclerosis comprising the step of administering to a patient, at least one dosage amount of a pharmaceutical composition comprising an effective non-toxic amount of each of a chelating agent, a non-steroidal anti-inflammatory drug (NSAID), an anti-oxidant and a form of hyaluronic acid, selected from the group consisting of hyaluronic acid and its non-toxic salts.

2. The method of claim 1 wherein the form of hyaluronic acid is sodium hyaluronate having a molecular weight less than about 750,000 daltons.

3. The method of claim 2 wherein the at least one dosage amount comprising a plurality of dosage amounts administered intravenously at suitable intervals over a period of time.

4. The method of claim 3 wherein the chelating agent is EDTA.

5. The method of claim 3 wherein the NSAID is selected from the group consisting of diclofenac, tromethamine salt of ketoralac, indomethacin, piroxicam, and ibuprofen.

6. The method of claim 3 wherein the anti-oxidant is Vitamin C.

7. The method of claim 2 wherein the at least one such dosage amount comprises (i) about 1–3 gm of the chelating agent/70 kg person;

(ii) about 15–30 mg of an NSAID;

(iii) about 12–50 gm anti-oxidant; and (iv) between about 50 mg to well in excess of 1000 mg of the form of hyaluronic acid;

in sterile water.

8. The method of claim 3 wherein the at least one such dosage amount comprises (i) about 1–3 gm of the chelating agent/70 kg person;

(ii) about 15–30 mg of an NSAID;

(iii) about 12–50 gm anti-oxidant; and (iv) between about 50 mg to well in excess of 1000 mg of the form of hyaluronic acid;

in sterile water.

9. The method of claim 7 or 8 wherein the chelating agent is EDTA.

10. The method of claim 7 or 8 wherein the NSAID is selected from the group consisting of diclofenac sodium and tromethamine salt of ketoralac.

11. The method of claim 7 or 8 wherein the anti-oxidant is selected from 12.5 to 25 gm of Vitamin C.

12. The method of claim 7 or 8 wherein the amount of sodium hyaluronate exceeds 200 mg.

13. The method of claim 7 or 8 wherein the amount of sodium hyaluronate is about 100 to about 120 mg, and the sodium hyaluronate has a molecular weight of about 150,000–225,000 daltons.

14. The method of claim 7 or 8 wherein the dosage amount further comprises 200 ml of sterile water.

15. The method of claim 7 or 8 wherein the dosage amount further comprises an effective amount of a local anesthetic.

16. The method of claim 15 wherein the dosage amount further comprises an effective amount of bicarbonate of soda.

\* \* \* \* \*